(12) United States Patent  
Curtis et al.

(10) Patent No.: US 11,869,334 B2  
(45) Date of Patent: Jan. 9, 2024

(54) MEDICAL ITEM DISTANCE ALERT SYSTEM

(71) Applicants: Mark Curtis, Stockton, CA (US); Kenya King, Stockton, CA (US)

(72) Inventors: Mark Curtis, Stockton, CA (US); Kenya King, Stockton, CA (US)

(*) Notice: Subject to any disclaimer, the term of this patent is extended or adjusted under 35 U.S.C. 154(b) by 84 days.

(21) Appl. No.: 17/204,722

(22) Filed: Mar. 17, 2021

(65) Prior Publication Data

US 2022/0301409 A1  Sep. 22, 2022

(51) Int. Cl.
  *G08B 21/24* (2006.01)
  *G08B 25/12* (2006.01)
  *G08B 25/00* (2006.01)
  *H04W 4/02* (2018.01)
  *H04W 4/12* (2009.01)
  *H04W 4/80* (2018.01)
  *H04W 4/90* (2018.01)
  *G06K 7/10* (2006.01)
  *G06F 1/16* (2006.01)

(52) U.S. Cl.
  CPC .............. *G08B 21/24* (2013.01); *G06F 1/163* (2013.01); *G06K 7/10306* (2013.01); *G08B 25/008* (2013.01); *G08B 25/12* (2013.01); *H04W 4/023* (2013.01); *H04W 4/12* (2013.01); *H04W 4/80* (2018.02); *H04W 4/90* (2018.02)

(58) Field of Classification Search
  CPC ...... G08B 21/24; G08B 25/008; G08B 25/12; G06F 1/163; G06K 7/10306; H04W 4/023; H04W 4/12; H04W 4/80; H04W 4/90
  See application file for complete search history.

(56) References Cited

U.S. PATENT DOCUMENTS

| 7,034,684 B2* | 4/2006 | Boman ............. G08B 13/1427 340/568.1 |
| 7,602,275 B2 | 10/2009 | Dishongh et al. |
| 8,378,812 B2 | 2/2013 | Choi et al. |
| 8,810,392 B1* | 8/2014 | Teller .................... G08B 21/24 340/572.1 |

(Continued)

FOREIGN PATENT DOCUMENTS

| GB | 2409084 A | 6/2005 |
| WO | 2017049493 A1 | 3/2017 |
| WO | WO-2021211542 A1 * | 10/2021 |

*Primary Examiner* — Adnan Aziz
(74) *Attorney, Agent, or Firm* — Outlier Patent Attorneys, PLLC (57) ABSTRACT

A mobile device can wirelessly connect, using transceivers, to a medical item and a wristband worn by a user. The mobile device includes a software application enabling a user to input distance thresholds. The wristband can also include a software application enabling a user to input distance thresholds. Both the mobile device application and the wristband application can monitor signals between the medical item and wristband. In another system, a medical item distance alert system can include a plurality of medical items. In another system, a mobile device is not in communication with the wristband or medical items. The wristband software application can monitor signals between medical items and provide alerts in the absence of another mobile device. Preferably, ultra-wideband (UWB) and Bluetooth transceivers can be implemented to provide accurate distance estimates with low power usage.

15 Claims, 5 Drawing Sheets

(56) References Cited

U.S. PATENT DOCUMENTS

| | | | |
|---|---|---|---|
| 9,901,515 B2 | 2/2018 | Roberts et al. | |
| 9,997,039 B1* | 6/2018 | Heaton | G08B 21/24 |
| 10,096,225 B2* | 10/2018 | Thomas | G07C 9/257 |
| 10,149,109 B2* | 12/2018 | Nishitani | H04W 4/80 |
| 10,332,375 B1* | 6/2019 | Gonzalez | G08B 21/0252 |
| 10,395,499 B2 | 8/2019 | Kritzler | G06Q 50/265 |
| 10,567,566 B2* | 2/2020 | Xue | H04L 67/52 |
| 10,580,284 B2* | 3/2020 | Ramaci | A61J 7/0454 |
| 10,885,759 B1* | 1/2021 | Lee | G08B 21/0453 |
| 11,120,671 B2* | 9/2021 | Grom | A41D 1/002 |
| 11,189,148 B2* | 11/2021 | Reeder | G08B 21/0286 |
| 2006/0089542 A1* | 4/2006 | Sands | A61B 5/0022 600/300 |
| 2008/0061993 A1* | 3/2008 | Fong | G08B 21/02 340/573.4 |
| 2011/0025493 A1* | 2/2011 | Papadopoulos | G08B 21/0453 340/539.12 |
| 2013/0141233 A1* | 6/2013 | Jacobs | G16H 20/40 340/521 |
| 2014/0159912 A1* | 6/2014 | Fraden | G16H 40/67 340/870.02 |
| 2014/0243749 A1* | 8/2014 | Edwards | H04B 1/3827 455/73 |
| 2014/0247154 A1* | 9/2014 | Proud | H02J 50/80 340/870.09 |
| 2014/0278523 A1* | 9/2014 | Vaglio | A61B 5/7465 340/539.12 |
| 2014/0308930 A1* | 10/2014 | Tran | H04W 4/50 455/414.1 |
| 2015/0017951 A1* | 1/2015 | Agrawal | H04W 76/14 455/411 |
| 2015/0242665 A1* | 8/2015 | Antonescu | G06K 19/0724 340/8.1 |
| 2015/0254424 A1 | 9/2015 | Zehler | |
| 2015/0269827 A1* | 9/2015 | Hopkins | G08B 21/0446 340/539.12 |
| 2016/0247378 A1* | 8/2016 | Baczuk | G08B 21/0266 |
| 2017/0109985 A1* | 4/2017 | Jenkins | G08B 21/0244 |
| 2018/0075721 A1* | 3/2018 | Oliver | G08B 21/24 |
| 2018/0280245 A1* | 10/2018 | Khalid | A61J 7/04 |
| 2018/0325426 A1* | 11/2018 | Shaw | G16H 40/67 |
| 2019/0213860 A1* | 7/2019 | Shaprio | H04W 4/029 |
| 2019/0365334 A1* | 12/2019 | Blanchard | A61B 5/7465 |
| 2020/0359944 A1* | 11/2020 | Raisoni | A61B 5/7405 |
| 2021/0150878 A1* | 5/2021 | Rodney | G08B 13/24 |
| 2022/0051542 A1* | 2/2022 | Alvarez | G08B 21/0283 |

* cited by examiner

MEDICAL ITEM DISTANCE ALERT SYSTEM

CROSS-REFERENCE TO RELATED APPLICATIONS

This is a Nonprovisional U.S. Patent Application under 35 U.S.C. 111.

BACKGROUND OF THE INVENTION

1. Field of the Invention

The present invention relates to systems and methods for medical alerts. More specifically, the invention relates to systems and methods for providing alerts to users when they travel a distance threshold away from medical items.

2. Description of Related Art

In the field of medical alerts, there are reminder systems that notify users when it is time to take medications. There are also systems employing transceivers attached to medication boxes to communicate with radio frequency devices. Present systems fail to disclose software installed on mobile devices and wristbands enabling a user to input a distance threshold and providing an alert signal to a user when the user reaches the distance threshold away from the medical item. Present systems also do not utilize ultra-wideband (UWB) transceivers for providing accurate distance estimation. Further, these systems also fail to disclose waterproof user wristbands with an emergency location button designed to be worn continuously by users.

There is a need in the field of medical item alerts for a system and method with transceivers embedded into medical items, a mobile device, a wristband, and software applications monitoring distance to provide timely alerts to a user who travels and forgets to bring important medical items.

SUMMARY OF THE INVENTION

In an example embodiment system and method, a mobile device (e.g. smartphone, tablet) can wirelessly connect, using transceivers, to a medical item and a wristband (e.g. smart bracelet) worn by a user. The wristband is designed to be worn continuously by a user so it can be made water-resistant or waterproof for wear in a shower or bathtub. The mobile device includes a software application enabling a user to input distance thresholds. The mobile device software application can monitor signals between the medical item and wristband. Further, the wristband can also include a software application enabling a user to input distance thresholds. The wristband software application can monitor signals between the medical item and wristband. If the user wearing the wristband travels a distance away from the medical item equal to or greater than the distance threshold, the software application communicates a first alert signal to the mobile device. The mobile device then transmits a second alert signal to the wristband. The wristband and mobile device can both provide alerts to the user that can be audible, visual (e.g. flashing light), and/or physical (e.g. vibrations).

In other systems and methods, a medical item distance alert system can include a plurality (two or more) of medical items. A first medical item includes a transceiver for transmitting and receiving signals between the wristband and first medical item. A second medical item includes a transceiver for transmitting and receiving signals between the wristband and second medical item. The software application can monitor signals between the first medical item and wristband, and the second medical item and wristband, providing alerts when distance thresholds are reached.

In further systems and methods, a mobile device is not in communication with the wristband or medical items. For example, the situation could occur if a user's mobile device is powered off, the mobile device software application is not operating, or if the user does not have a mobile device. The wristband can be a smart wristband with a transceiver and at least a memory, processor, and power source. Further, the smart wristband includes a software application enabling a user to input distance thresholds. The wristband software application can monitor signals between medical items and provide alerts.

Preferably, ultra-wideband (UWB) and Bluetooth transceivers can be implemented to provide accurate distance estimates with low power usage. Other communication may be used including but not limited to: 802.11 wireless network protocol; 802.15.4 protocol; infrared data transfer; acoustic coupler; or RFID.

These and other features and advantages will be apparent from reading of the following detailed description and review of the associated drawings. It is to be understood that both the forgoing general description and the following detailed description are explanatory and do not restrict aspects as claimed.

DETAILED DESCRIPTION OF THE INVENTION

The following descriptions relate principally to preferred embodiments while a few alternative embodiments may also be referenced on occasion, although many other alternative embodiments would also fall within the scope of the invention. The embodiments disclosed are not to be construed as describing limits to the invention, whereas the broader scope of the invention should instead be considered with reference to the claims, which may be now appended or may later be added or amended in this or related applications. Unless indicated otherwise, it is to be understood that terms used in these descriptions generally have the same meanings as those that would be understood by persons of ordinary skill in the art. It should also be understood that terms used are generally intended to have the ordinary meanings that would be understood within the context of the related art, and they generally should not be restricted to formal or ideal definitions, conceptually encompassing equivalents, unless and only to the extent that a particular context clearly requires otherwise. Considering the present disclosure, those of ordinary skill in the art should also appreciate that many changes can be made relative to the disclosed embodiments while still obtaining a comparable function or result without departing from the spirit and scope of the disclosure.

For purposes of these descriptions, a few wording simplifications should also be understood as universal, except to the extent otherwise clarified in a particular context either in the specification or in particular claims. The use of the term "or" should be understood as referring to alternatives, although it is generally used to mean "and/or" unless explicitly indicated to refer to alternatives only, or unless the alternatives are inherently mutually exclusive. Furthermore, unless explicitly dictated by the language, the term "and" may be interpreted as "or" in some instances. When referencing values, the term "about" may be used to indicate an approximate value, generally one that could be read as being that value plus or minus half of the value. "A" or "an" and the like may mean one or more, unless clearly indicated otherwise. Such "one or more" meanings are most especially intended when references are made in conjunction with open-ended words such as "having," "comprising" or "including." Likewise, "another" object may mean at least a second object or more. Thus, in the context of this specification, the term "comprising" is used in an inclusive sense and thus should be understood as meaning "including, but not limited to." As used herein, the use of "may" or "may be" indicates that a modified term is appropriate, capable, or suitable for an indicated capacity, function, or usage, while considering that in some circumstances the modified term may sometimes not be appropriate, capable, or suitable.

Generally, software are program modules include routines, programs, components, data structures, and other types of structures that perform particular tasks or implement particular abstract data types. A computing device, as used herein, refers to a device comprising at least a memory and a processor. A "computing device" is defined as including mobile phones, smartphones, tablets, smart watches, smart wristbands, laptops, and any other computing device able to support the features described herein. A "medical item" can include wearable medical devices and medications such as pills, insulin, inhalers, epinephrine, and the like. The terms "embed" and "affix" are used interchangeably in the disclosure to describe the same process. "Plurality" refers to two or more devices or components. Any "examples" described herein are non-limiting.

Most smartphones have Bluetooth transceivers and newer phones by Apple and Samsung also have ultra-wideband (UWB) transceivers. The newer Bluetooth Core Specification v5.1 ("Bluetooth 5.1") has improved technology enabling more accurate location tracking. Bluetooth Low Energy (BLE) beacons are commonly used transceivers for tracking items.

Figure 1:
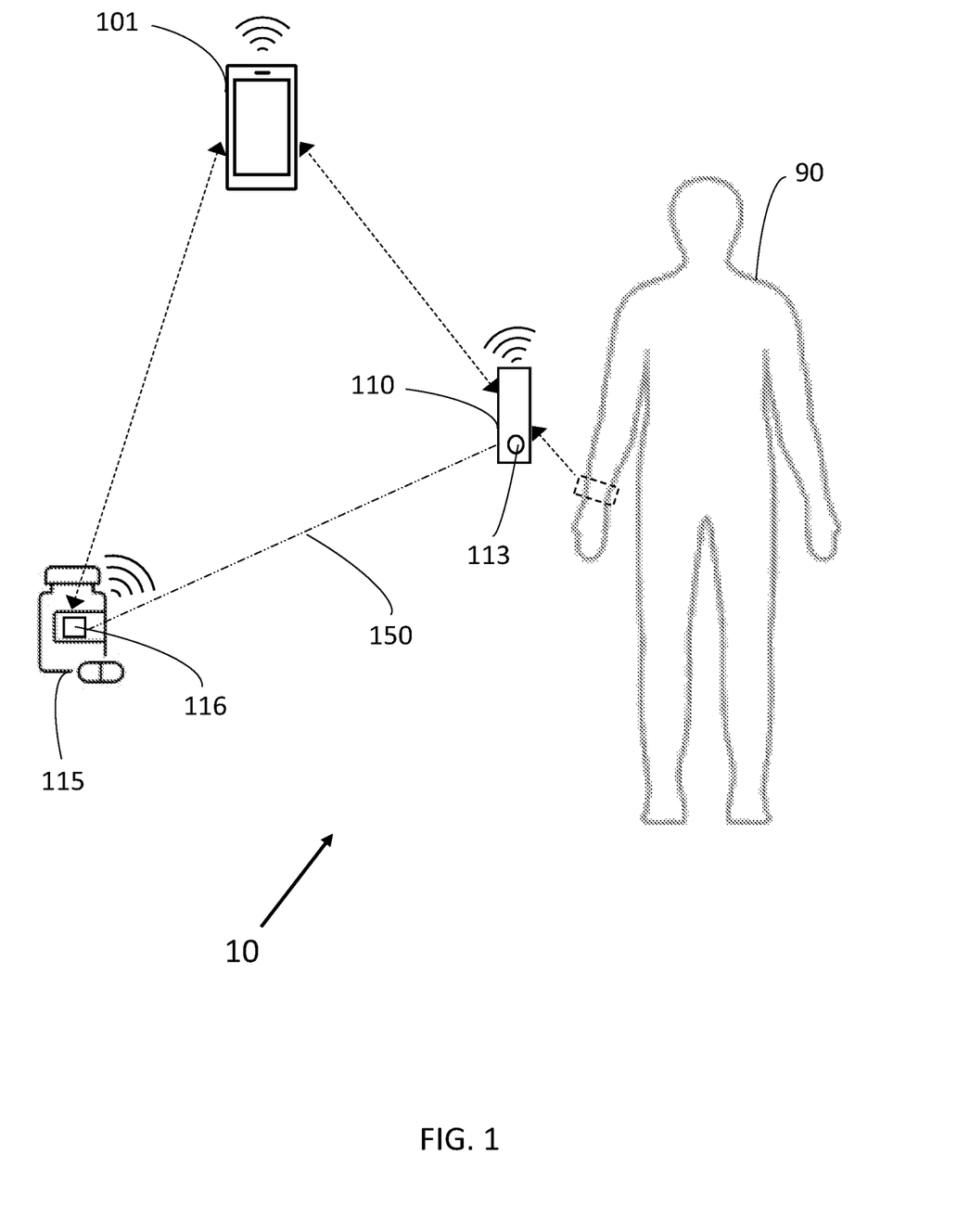
FIG. 1 illustrates an example embodiment of a medical item distance alert system.

FIG. 1 illustrates an example embodiment of a medical item distance alert system 10. A mobile device (e.g. smartphone, tablet) 101 can wirelessly connect to a medical item 115 and a wristband (e.g. smart bracelet) 110 worn by a user 90. The medical item 115 includes a transceiver 116 for transmitting and receiving signals between the wristband 110 and medical item 115. Further, the transceiver 116 can also transmit and receive signals from the mobile device 101. However, it is not necessary for the medical item 115 and mobile device 101 to communicate directly. For the mobile device 101, wristband 110, and medical item 115 to communicate with each other, they of course need to transmit signals in the same radio frequency range. For example, the three devices (101, 110, 115) could all have Bluetooth transceivers or UWB transceivers. Each device could also have both Bluetooth and UWB transceivers enabling communication in different frequency ranges.

The wristband 110 is a smart wristband with a transceiver 112 and at least a memory, processor, and power source. The wristband 110 can further include an emergency location button 113. When pressed, the emergency location button 113 can transmit a signal to the transceiver 116 of a medical item 115. The medical item 115 can further include an audio speaker. When the signal from the emergency location button 113 is received by the transceiver 116, a speaker installed in the medical item 115 can emit a sound enabling a user to locate the medical item 115. The wristband 110 is a smart wristband with a transceiver 112 and at least a memory, processor, and power source. The wristband 110 can further include an emergency location button 113. When pressed, the emergency location button 113 can transmit a signal to a transceiver 116 embedded in a medical item 115. Further, the wristband 110 is designed to be worn continuously by a user 90 so it can be made water-resistant or waterproof for wear in a shower or bathtub. The mobile device 101 includes a software application enabling a user to input distance thresholds. The software application can monitor signals between the medical item 115 and wristband 110.

Further, the wristband 110 is designed to be worn continuously by a user 90 so it can be made water-resistant or waterproof for wear in a shower or bathtub. The mobile device 101 includes a software application enabling a user to input distance thresholds. The software application can monitor signals between the medical item 115 and wristband 110.

An estimated distance between a medical item 115 and a wristband 110 worn by a user 90 can be determined using various techniques. For UWB communication, the distance between two UWB devices can be measured precisely by measuring the Time of Flight ("ToF") that it takes for a radio wave to pass between the two devices. ToF distance-based measurement enables precise centimeter-level accuracy. It delivers much more precise distance measurement than signal-strength estimation. UWB signals maintain their integrity and structure even in the presence of noise and multi-path effects. The nature of noise does not inhibit the distinctiveness of the short burst of signal. Further, due to the shortness of the radio pulse, multi-path effects will typically not overlap with the true signal, thus not damaging the integrity and strength of the true signal.

In another example, a received signal strength indicator ("RSSI") measurement between devices is commonly used to estimate distance between Bluetooth devices. Bluetooth 5.1 has a direction-finding ability enabling the system to calculate the direction of a Bluetooth signal via Angle of Arrival ("AoA"), which can be used along with detected RSSI to determine and track the location of devices and assets. To find direction, a mobile device with a single antenna, such as a wristband 110, can transmit to a fixed BLE sensor (e.g. medical item 115) with a multi-antenna array. The phase shift of the multiple antennas is measured to determine the angle of approach of the transmitting wristband 110. Combined with RSSI, the AoA is used to generate device location to centimeter-level accuracy. Other communication may be used including but not limited to: 802.11 wireless network protocol; 802.15.4 protocol; infrared data transfer; acoustic coupler; or RFID.

Figure 4:
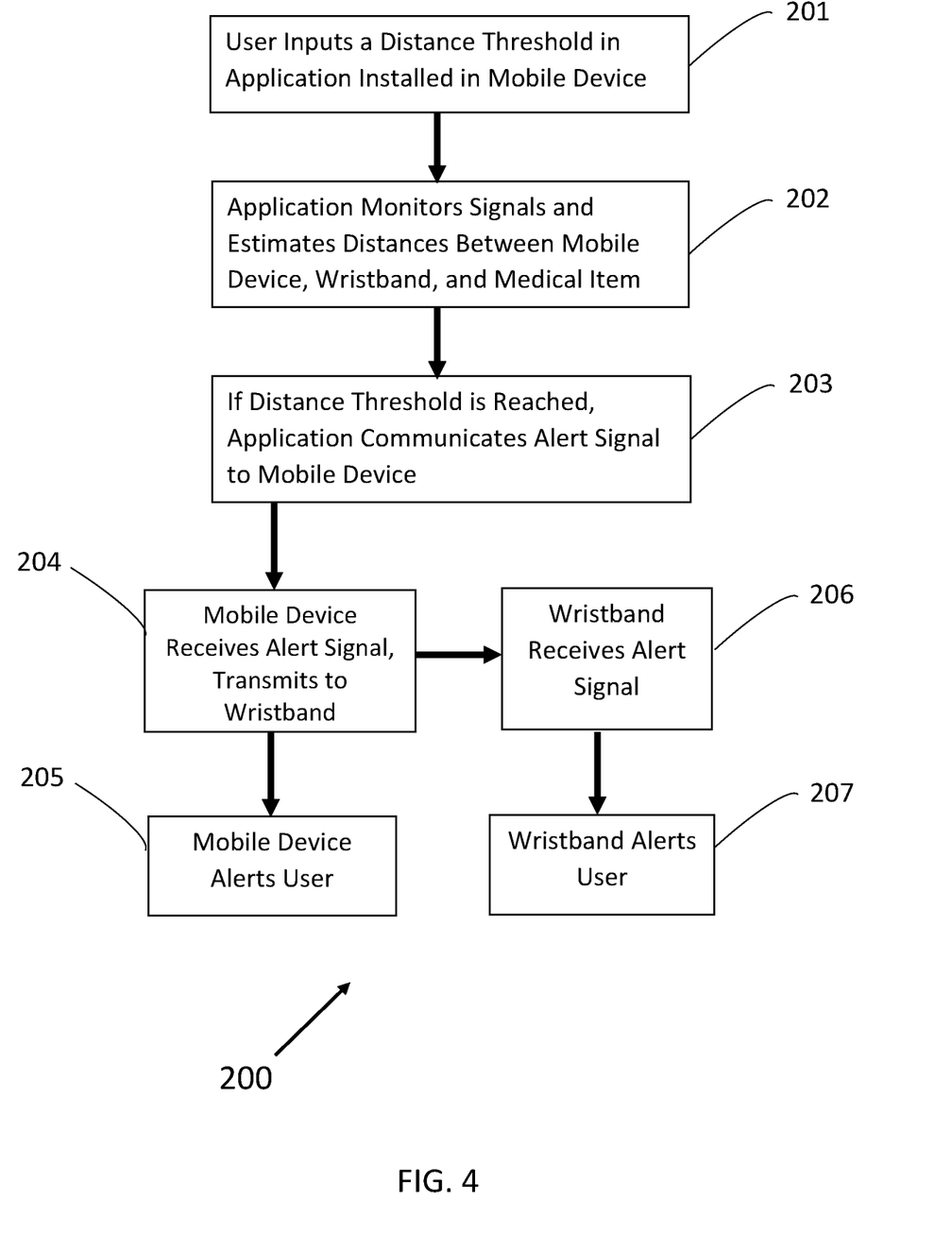
FIG. 4 illustrates a logic flow diagram of a method for providing an alert when a mobile device and wristband are in communication with a medical item.
Figure 5:
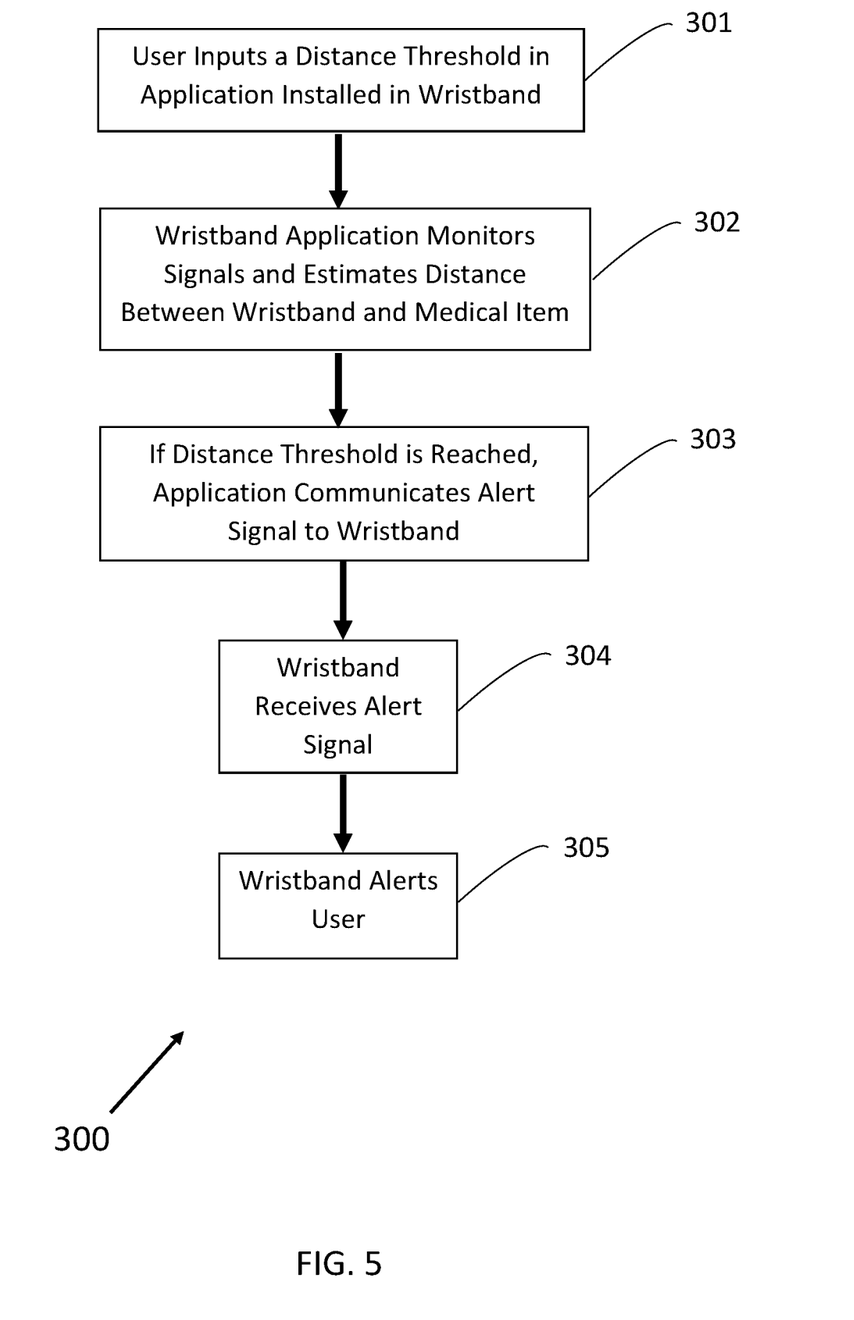
FIG. 5 illustrates a logic flow diagram of a method for providing an alert when a wristband is in communication with a medical item.

If the user 90 wearing the wristband 110 travels a distance 150 away from the medical item 115 equal to or greater than the distance threshold 120, the software application communicates a first alert signal to the mobile device 101. The mobile device 101 then transmits a second alert signal to the wristband 110. The wristband 110 and mobile device 101 can both provide alerts to the user that can be audible, visual (e.g. flashing light), and/or physical (e.g. vibrations). The alerts can be deactivated by the user manually on the software application or by manually pressing a button on the wristband 110. The alerts can be deactivated automatically by the application if the user 90 travels a distance 150 closer to the medical item 115 and less than the distance threshold 120. FIG. 4 and FIG. 5 of the present application and their corresponding detailed description provide greater details regarding the process and methods of communication.

If the wristband 110 stops receiving a signal from the mobile device 101, the wristband 110 can provide an alert to the user that can be audible, visual (e.g. flashing light), and/or physical (e.g. vibrations). For example, the situation could occur if a user's mobile device 101 is powered off, the mobile device software application is not operating, the mobile device 101 is too far away from the wristband 110, or the signal is poor due to interference. Further, the smart wristband 110 can include a software application enabling a user to input distance thresholds. The wristband software application can monitor signals between the medical item 115 and wristband 110.

Figure 2:
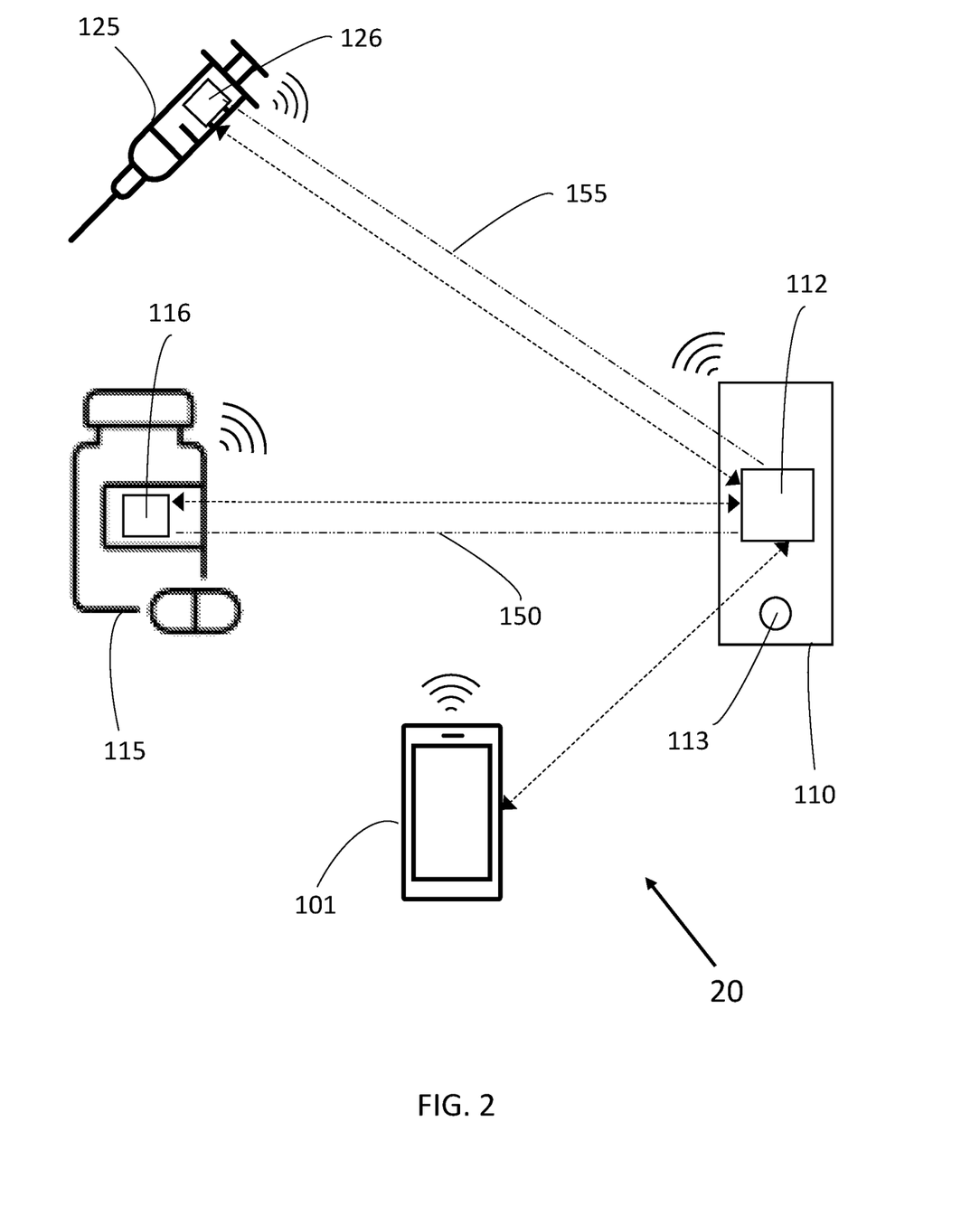
FIG. 2 illustrates an example embodiment of a medical item distance alert system with a plurality (two or more) of medical items.

FIG. 2 illustrates an example embodiment of a medical item distance alert system 20 with a plurality (two or more) of medical items. A mobile device 101 can wirelessly connect to a wristband 110 worn by a user 90. A first medical item 115 includes a transceiver 116 for transmitting and receiving signals between the wristband 110 and first medical item 115. A second medical item 125 includes a transceiver 126 for transmitting and receiving signals between the wristband 110 and second medical item 125. A software application can monitor signals between the first medical item 115 and wristband 110, and the second medical item and wristband 110. The medical item transceivers are preferably designed to consume low power and can be powered by coin cell batteries for example.

It is not necessary for the medical items 115, 125 to communicate directly with the mobile device 101. For example, the medical items 115, 125 and wristband 110 could have UWB transceivers. The wristband 110 could also have a Bluetooth transceiver. A user 90 could have a mobile device 101 with only Bluetooth but not UWB. In this example, the medical items 115, 125 and wristband 110 can communicate using UWB frequencies, while the wristband 110 and the mobile device 115 can communicate using Bluetooth frequencies. The distance 150 between the wristband 110 and the first medical item 115 can be estimated by the wristband 110 using a method such as TOF. In a similar manner, the distance 155 between the wristband 110 and the second medical item 125 can be estimated. The distance information can then be transmitted from the wristband 110 to the mobile device 101. Although only two medical items 115, 125 are shown in FIG. 2, systems with more than two medical items are contemplated in the scope of this invention.

Figure 3:
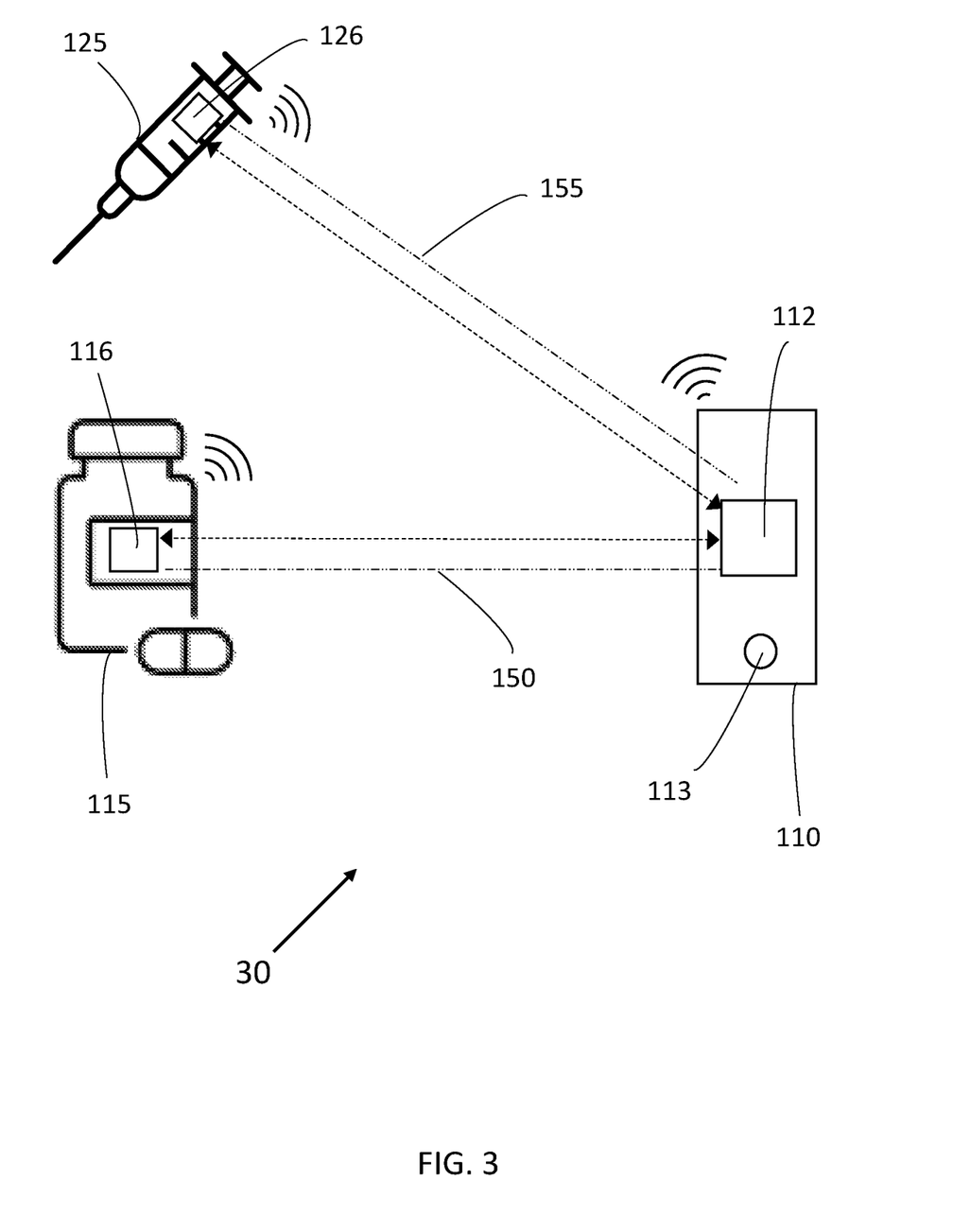
FIG. 3 illustrates an example embodiment of a medical item distance alert system.

FIG. 3 illustrates an example embodiment of a medical item distance alert system 30. In this system 30, a mobile device 101 is not in communication with the wristband 110 or medical items 115, 125. For example, the situation could occur if a user's mobile device 101 is powered off, the mobile device software application is not operating, or if the user 90 does not have a mobile device 101. The wristband 110 is a smart wristband with a transceiver 112 and at least a memory, processor, and power source. Further, the smart wristband 110 includes a software application enabling a user to input distance thresholds. The software application can monitor signals between the first medical item 115 and wristband 110, and the second medical item and wristband 110.

FIG. 4 illustrates a logic flow diagram of a method 200 for providing an alert when a mobile device 101 and wristband 110 are in communication with a medical item 115. In the first step 201, the user 90 can input (201) a distance threshold 120 on the application installed on the mobile device 101. This distance threshold 120 can be selected from a range and is based on a user's preference for receiving alerts. Once the distance threshold 120 is inputted (step 201) and stored in the application, the application monitors (step 202) the communication link between a mobile device 101, wristband 110, and medical item 115. In step 203, if the user 90 wearing the wristband 110 travels a distance away from the medical item 115 equal to or greater than the distance threshold 120, the application communicates alert signals to the mobile device 101 and the wristband 110. In step 204, the mobile device 101 receives an alert signal, alerts (step 205) the user 90, and transmits the alert signal to the wristband 110. The alert (step 205) can be audible, visual (e.g. flashing light), and/or physical (e.g. vibrations). The alert (step 205) can be active continuously until the user 90 deactivates it or the alert (205) can be active at time intervals (e.g. three seconds) until deactivated. The alert (205) can also be deactivated automatically by the application if the user 90 travels a distance closer to the medical item 115 less than the distance threshold 120. In step 206, the wristband 110 receives an alert signal and alerts (step 207) the user 90. The alert (step 207) can be audible, visual, and/or physical. The alert (step 207) can be active continuously until the user 90 deactivates it or the alert (207) can be active at time intervals until deactivated. The alert (207) can also be deactivated automatically by the application if the user 90 travels a distance closer to the medical item 115 less than the distance threshold 120.

FIG. 5 illustrates a logic flow diagram of a method 300 for providing an alert when a wristband 110 is in communication with a medical item 115. In this instance, the mobile device 101 is not in communication with the wristband 110 or medical item 115. For example, the situation could occur if a user's mobile device 101 is powered off, the mobile device application is not operating, or if the user 90 does not have a mobile device 101. In the first step 301, the user 90 can input (301) a distance threshold 120 on the application installed on the wristband 110. This distance threshold 120 can be selected from a range and is based on a user's preference for receiving alerts. Once the distance threshold 120 is inputted (step 301) and stored in the application, the application monitors (step 302) the communication link between the wristband 110 and medical item 115. In step 303, If the user 90 wearing the wristband 110 travels a distance away from the medical item 115 equal to or greater than the distance threshold 120, the application communicates alert signals to the wristband 110. In step 304, the wristband 110 receives an alert signal and alerts (step 305) the user 90. The alert (step 305) can be audible, visual, and/or physical. The alert (step 305) can be active continuously until the user 90 deactivates it or the alert (305) can be active at time intervals until deactivated. The alert (305) can also be deactivated automatically by the application if the user 90 travels a distance closer to the medical item 115 less than the distance threshold 120.

The invention claimed is:

1. A medical item distance alert system comprising:
   a. a mobile device comprising a first transceiver and a software application;
   b. a wristband comprising a first transceiver;
   c. a first medical item comprising a first transceiver;
   d. wherein the software application is configured to receive and store a distance threshold inputted by a user;
   e. wherein the software application is configured to monitor signals between the first medical item and the mobile device and signals between the mobile device and the wristband as being worn by the user, to determine a distance between the first medical item and the wristband;
   f. wherein the software application is configured to communicate a first alert signal to the mobile device when the distance determined between the first medical item and the wristband exceeds the distance threshold;
   g. wherein the mobile device is configured to provide a first alert to the user, thereby indicating to the user of a separation between the user and the first medical item;
   h. wherein the mobile device is configured to transmit a second alert signal to the wristband being worn by the user;
   i. wherein the wristband is configured to provide a second alert to the user, thereby providing another indication to the user of the separation between the user and the first medical item;
   j. wherein the first alert and the second alert can be deactivated by the user on the software application; and
   k. wherein the first alert and the second alert can be deactivated automatically by the software application if the user travels a distance closer to the first medical item and less than the distance threshold.

2. The system of claim 1, wherein the first alert and the second alert can be deactivated by the user by manually pressing a button on the wristband.

3. The system of claim 1 wherein the first transceiver of the mobile device is a Bluetooth transceiver, the first transceiver of the wristband is a Bluetooth transceiver, and the first transceiver of the first medical item is a Bluetooth transceiver.

4. The system of claim 1 wherein the first transceiver of the mobile device is an ultra-wideband (UWB) transceiver, the first transceiver of the wristband is a UWB transceiver, and the first transceiver of the first medical item is a UWB transceiver.

5. The system of claim 1 wherein the wristband further comprises:
   a. a second transceiver;
   b. wherein the first transceiver of the wristband is a Bluetooth transceiver; and
   c. the second transceiver is an ultra-wideband (UWB) transceiver.

6. The system of claim 1 wherein the first medical item further comprises:
   a. a second transceiver;
   b. wherein the first transceiver of the first medical item is a Bluetooth transceiver; and
   c. the second transceiver is an ultra-wideband (UWB) transceiver.

7. The system of claim 1, wherein the wristband further comprises an emergency location button and the first medical item further comprises an audio speaker, such that the audio speaker emits a sound when the emergency location button is pressed.

8. The system of claim 1, further comprising:
   a. a plurality of medical items, including the first medical item; and
   b. wherein the software application is configured to monitor signals between each medical item of the plurality of medical items and the wristband, to determine separation distances between the wristband and each medical item of the plurality of medical items.

9. The system of claim 1, wherein the wristband further comprises:
   a. a software application;
   b. wherein the software application of the wristband is configured to receive and store a distance threshold inputted by the user;
   c. wherein the software application of the wristband is configured to monitor signals between the first medical item and the wristband to determine a separation distance between the first medical item and the wristband; and
   d. wherein the software application of the wristband is configured to communicate an alert signal to the wristband when the software application determines that the separation distance has exceeded the distance threshold.

10. A method for providing a medical item distance alert, comprising:
    a. providing a mobile device, the mobile device comprising a first transceiver and a software application;
    b. providing a wristband, the wristband comprising a first transceiver;
    c. providing a first medical item, the first medical item comprising a first transceiver;
    d. providing a software application configured to receive and store a distance threshold inputted by a user;
    e. inputting, by the user, a distance threshold into the software application;
    f. monitoring, by the software application, signals between the first medical item and the mobile device and signals between the mobile device and the wristband as being worn by the user, to determine a separation distance between the wristband and the first medical item;
    g. communicating, by the software application, a first alert signal to the mobile device when the separation distance is determined to exceed the distance threshold;
    h. receiving, by the mobile device, the first alert signal;
    i. providing, by the mobile device, a first alert to the user that the first medical item is separated from the user;
    j. transmitting, by the mobile device, a second alert signal to the wristband;
    k. receiving, by the wristband, the second alert signal; and
    l. providing, by the wristband, a second alert to the user, thereby providing a second alert signal to the user that the first medical item is separated from the user.

11. The method of claim 10:
    a. wherein the first alert and the second alert can be deactivated by the user on the software application;
    b. wherein the first alert and the second alert can be deactivated automatically by the software application if the user travels a distance closer to the first medical item and less than the distance threshold; and
    c. wherein the first alert and the second alert can be deactivated by the user by manually pressing a button on the wristband.

12. The method of claim 10, further comprising:
   a. providing a plurality of medical items, including the first medical item; and
   b. monitoring, by the software application, signals between each of the medical items in the plurality of medical items and the wristband, thereby permitting separation distances to be determined between each medical item of the plurality of medical items and the wristband.

13. The method of claim 10, wherein the first transceiver of the mobile device is a Bluetooth transceiver, the first transceiver of the wristband is a Bluetooth transceiver, and the first transceiver of the first medical item is a Bluetooth transceiver.

14. The method of claim 10, wherein the first transceiver of the mobile device is an ultra-wideband (UWB) transceiver, the first transceiver of the wristband is a UWB transceiver, and the first transceiver of the first medical item is a UWB transceiver.

15. The method of claim 10, wherein the wristband further comprises:
   a. a second transceiver;
   b. wherein the first transceiver of the wristband is a Bluetooth transceiver; and
   c. the second transceiver is an ultra-wideband (UWB) transceiver.

* * * * *